United States Patent
Martin et al.

(10) Patent No.: US 9,754,336 B2
(45) Date of Patent: Sep. 5, 2017

(54) GESTURE-BASED COMMUNICATION SYSTEMS AND METHODS FOR COMMUNICATING WITH HEALTHCARE PERSONNEL

(71) Applicant: Augment Medical, Inc., Raleigh, NC (US)

(72) Inventors: Timothy N. Martin, Raleigh, NC (US); Richard A. Daniels, Raleigh, NC (US); Andrew J. DiMeo, Sr., Raleigh, NC (US); Wenbo Sharon Zhang, Raleigh, NC (US); Xiaji Astor Liu, Raleigh, NC (US); Daniel Bieber, Raleigh, NC (US)

(73) Assignee: The Medical Innovators Collaborative, Raleigh, NC (US)

( * ) Notice: Subject to any disclaimer, the term of this patent is extended or adjusted under 35 U.S.C. 154(b) by 115 days.

(21) Appl. No.: 14/157,582

(22) Filed: Jan. 17, 2014

(65) Prior Publication Data

US 2014/0203931 A1    Jul. 24, 2014

Related U.S. Application Data

(60) Provisional application No. 61/754,003, filed on Jan. 18, 2013.

(51) Int. Cl.
*G08B 21/18* (2006.01)
*G06Q 50/22* (2012.01)

(52) U.S. Cl.
CPC .................................. *G06Q 50/22* (2013.01)

(58) Field of Classification Search
None
See application file for complete search history.

(56) References Cited

U.S. PATENT DOCUMENTS

| | | | | |
|---|---|---|---|---|
| 4,082,087 A | * | 4/1978 | Howson | A61B 5/04085 600/391 |
| 4,170,225 A | * | 10/1979 | Criglar | A61B 5/04017 482/900 |
| 4,213,466 A | | 7/1980 | Stulen | |

(Continued)

FOREIGN PATENT DOCUMENTS

JP    2004275527    10/2004

OTHER PUBLICATIONS

Tohru Yagi, "Eye-gaze Interfaces using Electro-oculograpgy (EOG)", EGIHMI 2010 Proceedings.

(Continued)

*Primary Examiner* — Toan N Pham
*Assistant Examiner* — Chico A Foxx
(74) *Attorney, Agent, or Firm* — Olive Law Group, PLLC

(57) ABSTRACT

Gesture-based communication systems and methods for communicating with healthcare personnel are disclosed. According to an aspect, a system is disclosed that includes a movement detector configured to detect movement of muscle and to generate a wireless signal in response to detection of the muscle movement. The system also includes a base station in wireless communication with the movement detector, and configured to implement a predetermined action based on the wireless signal. The base station may be configured to interface with a healthcare call system such as in a hospital environment. The base station may control the healthcare call system to communicate a notification signal based on the wireless signal.

30 Claims, 3 Drawing Sheets

(56) References Cited

U.S. PATENT DOCUMENTS

| | | | |
|---|---|---|---|
| 4,359,724 A | 11/1982 | Zimmerman et al. | |
| 5,808,552 A | 9/1998 | Wiley et al. | |
| 6,001,065 A * | 12/1999 | DeVito | G06F 3/015 340/4.11 |
| 6,076,011 A | 6/2000 | Hoover | |
| 6,254,536 B1 * | 7/2001 | DeVito | G06F 3/015 340/4.11 |
| 6,493,578 B1 | 12/2002 | DeFeo | |
| 6,560,798 B2 * | 5/2003 | Welling | A61G 7/05 248/694 |
| 6,636,763 B1 * | 10/2003 | Junker | G06F 3/013 340/4.11 |
| 9,055,071 B1 * | 6/2015 | Gates | H04L 63/1408 |
| 2001/0031916 A1 | 10/2001 | Bennet et al. | |
| 2002/0070866 A1 | 6/2002 | Newham | |
| 2002/0107436 A1 | 8/2002 | Barton et al. | |
| 2004/0034645 A1 | 2/2004 | Hiraiwa et al. | |
| 2004/0183684 A1 | 9/2004 | Callaway | |
| 2005/0137464 A1 | 6/2005 | Bomba | |
| 2006/0071934 A1 * | 4/2006 | Sagar | A61B 5/0488 345/473 |
| 2007/0060830 A1 | 3/2007 | Le et al. | |
| 2008/0004904 A1 * | 1/2008 | Tran | A61B 5/0006 705/2 |
| 2008/0083065 A1 | 4/2008 | Bautovich | |
| 2008/0188777 A1 | 8/2008 | Bedziouk et al. | |
| 2008/0266121 A1 * | 10/2008 | Ellul | G08B 7/066 340/584 |
| 2008/0272918 A1 | 11/2008 | Ingersoll | |
| 2008/0294019 A1 * | 11/2008 | Tran | A61B 5/0006 600/301 |
| 2009/0105788 A1 | 4/2009 | Bartol et al. | |
| 2009/0327171 A1 | 12/2009 | Tan et al. | |
| 2010/0174342 A1 | 7/2010 | Boston et al. | |
| 2010/0305467 A1 | 12/2010 | Rodilla Sala et al. | |
| 2012/0001846 A1 * | 1/2012 | Taniguchi | G06F 1/163 345/156 |
| 2012/0108221 A1 * | 5/2012 | Thomas | H04M 1/72522 455/415 |
| 2012/0289227 A1 * | 11/2012 | Dhodapkar | H04L 12/1827 455/435.1 |
| 2013/0012786 A1 * | 1/2013 | Horseman | G06F 19/3418 600/301 |
| 2014/0051044 A1 * | 2/2014 | Badower | A61B 5/00 434/236 |
| 2014/0062867 A1 * | 3/2014 | Baumgartner | G06F 3/013 345/156 |
| 2014/0235253 A1 * | 8/2014 | Li | H04L 65/1069 455/445 |

OTHER PUBLICATIONS

International Search Report and the Written Opinion for corresponding PCT application No. PCT/US2014/011960 dated May 15, 2014.

* cited by examiner

GESTURE-BASED COMMUNICATION SYSTEMS AND METHODS FOR COMMUNICATING WITH HEALTHCARE PERSONNEL

CROSS REFERENCE TO RELATED APPLICATION

This application claims the benefit of U.S. Provisional Patent Application Ser. No. 61/754,003, filed Jan. 18, 2013, the disclosure of which is incorporated herein by reference in its entirety.

TECHNICAL FIELD

The presently disclosed subject matter related to healthcare. More particularly, the presently disclosed subject matter relates to gesture-based communication systems and methods for communicating with healthcare personnel.

BACKGROUND

In the field of healthcare, communication failures have been identified as a top underlying cause of events resulting in death or serious injury to patients while under hospital care. In particular, communication between patient and caregiver is critical to timely assessment, accurate diagnosis, and proper treatment. When lapses in communication occur, patients may lose their "rights" to be informed of their medical status and to be involved in the decision making process of treatment. Furthermore, patient discomfort may increase, quality of life may decrease, hospital stays may be lengthened, and in some extreme cases, death may occur. Barriers to communication may occur in many forms, such as new physical disabilities caused by traumatic injury or preexisting cognitive disabilities. As many as 157,600 patients with common communication disabling disorders are treated in U.S. hospitals each year.

Within a hospital or assisted living facility, patients require access to nurse call equipment. Standard nurse call equipment, such as pillow speakers and call cords, require function of a patient's hands to activate. In many cases, these patients' specific disabilities do not allow them this function. The term "complex communications needs" (CCN) is commonly used to refer to the needs of such severely disabled patients. The importance of providing access to augmentative and alternative communication (AAC) equipment for patients with CCN to allow them to communicate with a nurse is well documented. Furthermore, studies have indicated that more reliable and effective nurse call equipment can both improve patient care and reduce the burden of care placed on nurses.

In response to the need for AAC, numerous commercial devices have been developed and research studies conducted. State of the art adaptive technologies for persons with CCN rely on some function of voluntary muscles innervated by cranial nerves. Of devices designed for hospital nurse call, inhalation and exhalation controlled sip-and-puff and pressure pad switches that are typically placed on the shoulder and activated by lateral head movements are the most common commercially available devices.

While existing technologies provide some relief for nurse call communication difficulties, the problem remains largely unresolved. Immobilized patients are frequently repositioned to prevent pressure sores, and others are mechanically ventilated or intubated with large masks over their face. Pressure switches are insensitive even when they work properly, but often fall or move on the patient. Access to the mouth for a sip-and-puff sensor is blocked by intubation or ventilation. Verbal communication is often impossible for this reason or due to an existing speech disability. Even eye tracking may require lengthy repositioning and setup of equipment with each change in the patient's position.

In view of the foregoing, it is desired to provide improved systems and methods for communicating with healthcare personnel.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Disclosed herein are gesture-based communication systems and methods for communicating with healthcare personnel. The systems disclosed herein can be rapidly deployed and reliably used by any patient who needs to communicate with healthcare personnel, such as a nurse. The systems and methods disclosed herein may provide a singular solution for all or most patients, even those with the most complicated communication barriers. The systems and methods disclosed herein may use any of various controlled movements of a patient as input. In an example, facial movement of a patient may be used as input for communication with healthcare personnel.

According to an aspect, a system is disclosed that includes a movement detector configured to detect movement of muscle and to generate a wireless signal in response to detection of the muscle movement. The system also includes a base station in wireless communication with the movement detector, and configured to implement a predetermined action based on the wireless signal. The base station may be configured to interface with a healthcare call system such as in a hospital environment. The base station may control the healthcare call system to communicate a notification signal based on the wireless signal. The base station may also connect to a third party wireless device such as a computer, smartphone, or alert system designed for use in a home or rehabilitation center.

BRIEF DESCRIPTION OF THE DRAWINGS

The foregoing summary, as well as the following detailed description of various embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings.

DETAILED DESCRIPTION

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Figure 1:
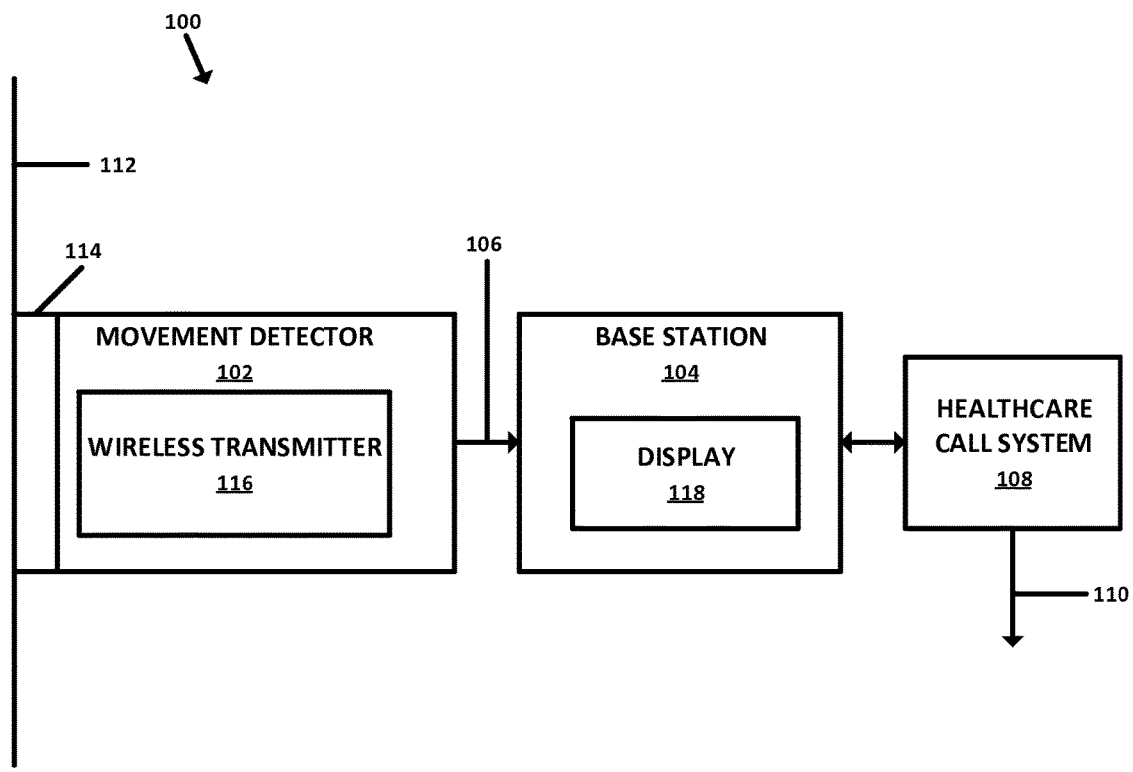
FIG. 1 is a block diagram of an example gesture-based system for communicating with healthcare personnel in accordance with embodiments of the present disclosure.

FIG. 1 illustrates a block diagram of an example gesture-based system 100 for communicating with healthcare personnel in accordance with embodiments of the present disclosure. Referring to FIG. 1, the system 100 includes a movement detector 102 and a base station 104. The movement detector may be configured to detect movement of muscle and to generate a wireless signal 106 in response to detection of the muscle movement. The base station 104 can be in wireless communication with the movement detector 102.

Further, the base station 104 may be configured to implement a predetermined action based on the wireless signal. For example, the base station 104 may recognize the wireless signal as being a request for assistance from healthcare personnel, such as a nurse or physician. In this example, the base station 104 may be interfaced with a healthcare call system 108, and may control the healthcare call system 108 to communicate a notification signal 110 based on the wireless signal 106. The notification signal 100 may be received at, for example, a nurse station and cause an alert or notification that a patient has requested attention.

In accordance with an embodiment, the movement detector 102 may be attached to or otherwise positioned near a skin surface 112 of a patient. Beneath the skin surface 112 is muscle, the movement of which can be detected by the movement detector 102. As an example, the muscle may be located in the forehead, biceps, forearm, or any other muscle, the movement of which can be detected. Thus, when a patient controls movement of the muscle, the movement can be interpreted as a control for causing the movement detector 102 to send the wireless signal 106 to the base station 104.

As an example, the movement detector 102 can be an electromyography device comprising adhesive coated electrodes 114 for attachment of the movement detector to the skin surface 112. The movement detector 102 can detect an electrical signal generated by contraction of the muscle. Further, the movement detector 102 can generate the wireless signal 106 in response to detection of the electrical signal. As an example, the movement detector 102 can include one or more electrodes configured to detect the electrical signal. The electrodes may be suitable spaced apart for detection of the electrical signal. In an example, the electrodes may be electrically connected to an amplifier for amplification of the electrical signal.

In accordance with an embodiment, the movement detector 102 includes a wireless radio transmitter 116 configured to communicate the wireless signal 106 to the base station 104. For example, the wireless radio transmitter 116 may receive an electrical signal representative of the detected movement. The wireless radio transmitter 116 may generate a digital signal value based on the electrical signal and communicate the digital signal value to the base station 104.

In accordance with an embodiment, the base station 104 may include a display 118 or suitable light emitter, such as a light emitting diode (LED), configured to emit light based on the wireless signal 106. In an example, the base station 104 may receive the wireless signal 106 and apply an algorithm, examples of which are described in further detail herein, to the data contained within the wireless signal 106. The base station 104 may control implementation of a predetermined action based on the application of the algorithm to the data. A predetermined action may include causing a light emitter to emit light or a display to display graphics or text for indicating that movement was detected and/or that a communication was sent via the healthcare call system 108. In another example, the predetermined action may be the sending of a message to the healthcare call system 108 for calling healthcare personnel.

Figure 2:
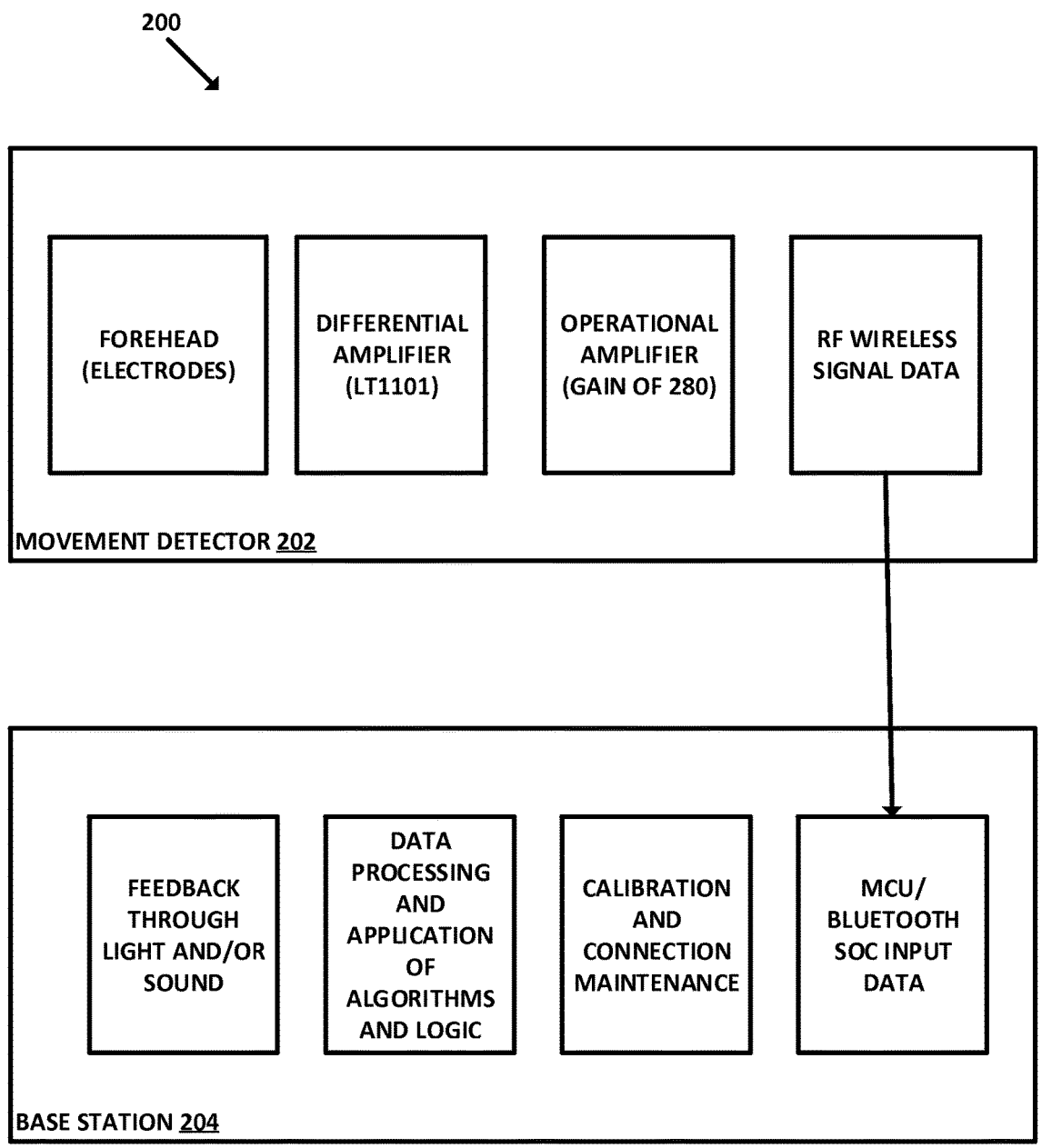
FIG. 2 is a block diagram of another example gesture-based system for communicating with healthcare personnel in accordance with embodiments of the present disclosure.

FIG. 2 illustrates a block diagram of another example gesture-based system 200 for communicating with healthcare personnel in accordance with embodiments of the present disclosure. Referring to FIG. 2, a facial electromyography sensor (or movement detector) 202 may be a wireless, disposable electromyography device that can be placed on a patient's forehead. The movement detector 202 can include circuitry configured to use an electromyography technique to capture the electrical signals generated by the user's muscle contractions, such as those of the frontalis muscle located in the forehead. In an alternative, the movement detector 202 may use the same or a similar technique to capture signals from different muscles or muscle groups in various anatomical locations.

In accordance with embodiments of the present disclosure, the movement detector 202 may include multiple electrodes in contact with the patient's forehead and over a target muscle or muscle group for conducting the electrical activity generated by the muscle(s). In an example, the movement detector 202 may include 3 or more electrodes that are suitably spaced apart.

The movement detector 202 may include an instrumentation amplifier composed of an instrumentation amplifier, operational amplifiers, capacitors, diodes and resistors which takes a differential reading from the electrodes and amplifies the signal. Further, the movement detector may include a wireless radio transmitter which may use a radio frequency, such as BLUETOOTH®, ZIGBEE®, or SNAP®, wireless technique or another suitable technique or protocol to transmit a digital signal value to a remote receiver not contained within the movement detector 202. In addition, the movement detector can include a coin cell lithium battery that provides power for the electromyography sensor as well as the wireless radio. Further, the movement detector 202 may include a thin, flexible packaging made of a medical grade disposable components with an adherent material on one side containing the requisite electrodes. This shielding may be in various shapes, but generally resembles an adhesive bandage such as the adhesive bandage referred to as a "Band-Aid". This shielding or a porous material may insulate an electrode surface from electronic, absorb bodily fluids that may interfere with signal conduction, and/or allow for an elastic characteristic in the sensor or detector. All electrical components defined above may be contained within this component.

The system may include a base station 204 that can be an electromyography device configured to receive a wireless radio signal from the movement detector 202. The base station 204 may interface with a suitable jack (e.g., a ¼" jack) located on and interfaced with a nurse call wall unit (or suitable healthcare call system) to transmit a call signal. The base station 204 may implement processing and calibration for the signal received and also provides visual and audio user feedback.

In accordance with embodiments, the base station 204 may include a wireless radio receiver which may use BLUETOOTH® wireless technique or another suitable technique or protocol for receiving a digital signal from a paired transmitter not contained within the base station device. The base station 204 may include a suitable plug (e.g., a ¼" plug) for transmitting a contact closure call signal through a suitable jack (e.g., a ¼" jack) not contained within the base station 204. Further, the base station 204 may include a lamp that is configured to project a visual symbol indicating nurse call activation. Further, the base station 204 may include a speaker configured to emit audio tones indicating device use and nurse call activation. The base station 204 may also include an LED for indicating calibration. Signal processing may be implemented by bandpass filters to filter incoming signal data and a microprocessor to determine output according to software algorithms. A housing may contain the components of the base station 204 for protecting the device from damage and providing a pleasing aesthetic appearance.

Figure 3:
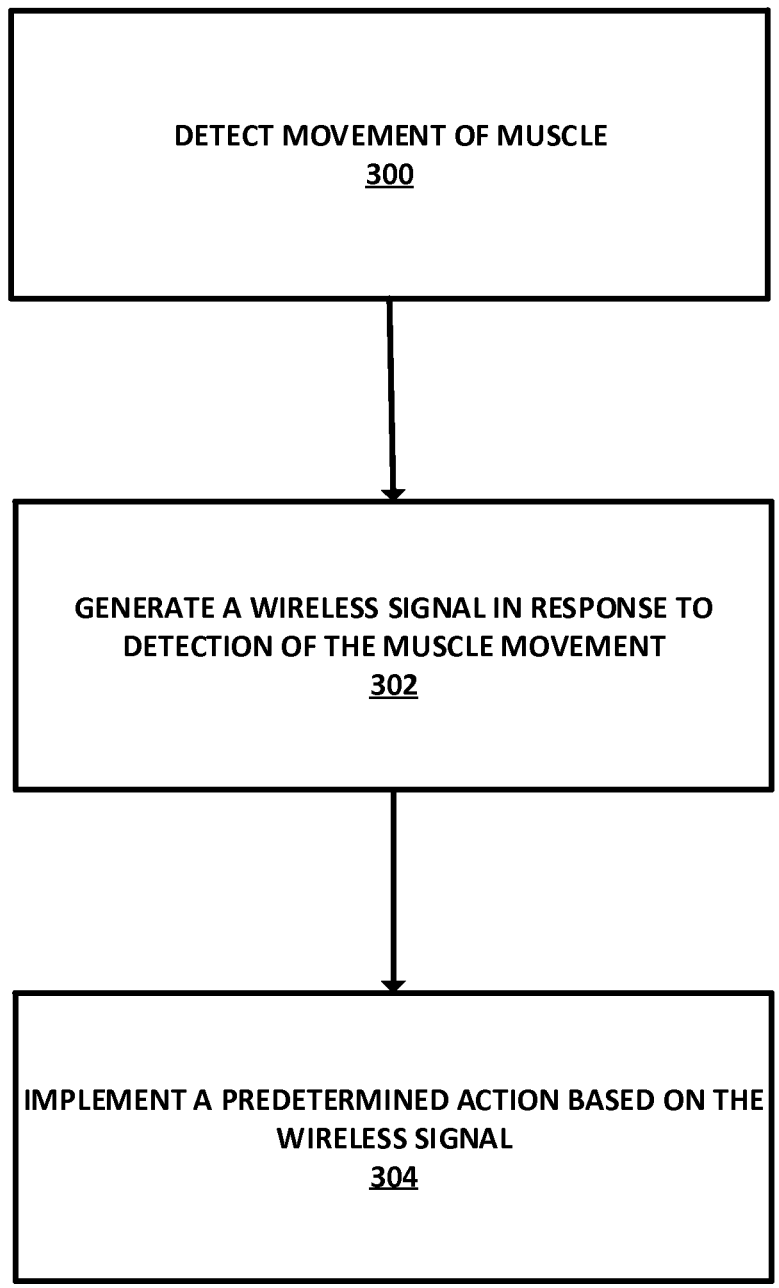
FIG. 3 is a flow chart of an example method for communicating with healthcare personnel in accordance with embodiments of the present disclosure.

FIG. 3 illustrates a flow chart of an example method for communicating with healthcare personnel in accordance with embodiments of the present disclosure. The method is described in this example as being implemented by the gesture-based system 100 shown in FIG. 1, although it should be understood that the method may alternatively be implemented by any suitable system. Referring to FIG. 3, the method includes detecting 300 movement of muscle. For example, the movement detector 102 shown in FIG. 1 may be attached to the skin surface 112, and may detect contraction of muscle therein.

The method of FIG. 3 includes generating 302 a wireless signal in response to detection of the muscle movement. Continuing the aforementioned example, the movement detector 102 may generate an electrical signal representative of the muscle contraction. The wireless radio transmitter 116 may communicate the wireless signal 106 to the base station. Subsequently, the wireless radio transmitter 116 may receive an electrical signal representative of the detected movement. The wireless radio transmitter 116 may generate a digital signal value based on the electrical signal and communicate the digital signal value to the base station 104.

The method of FIG. 3 includes implementing 304 a predetermined action based on the wireless signal. Continuing the aforementioned example, the base station 104 may emit light based on the wireless signal 106. A predetermined action may include causing a light emitter to emit light or a display to display graphics or text for indicating that movement was detected and/or that a communication was sent via the healthcare call system 108. In another example, the predetermined action may be the sending of a message to the healthcare call system 108 for calling healthcare personnel.

In accordance with embodiments, the base station, such as base station 104 shown in FIG. 1, may implement calibration. Calibration may be for a period of 5 seconds or any other suitable time length. In an example, the base station may include suitable hardware, software, firmware, or combinations thereof for implementing calibration or other functions described herein. During calibration, the maximum and minimum values recorded during the 5 second period may be recorded from the analog-to-digital converter (ADC). The recorded maximum and minimum values may be applied as the absolute maximum and minimum values of the system. In an example, the recorded values may be MAX 750 MIN 300, and then the absolute values are MAX 1023 MIN 0. A signal of 700 can be understood by software as 909 (e.g., ((700−300)/(750−300))*1023=909).

The system may also implement a suitable smoothing technique. For example, an array of recorded values may be created from the ADC. Current designs instruct 20 data points to be stored. Each time the ADC reads a new data point, one value may be added to the array at the beginning of the array, and one value may be removed from the array. Subsequently, averaging may be implemented, which may include adding the values up in the array at any one time and then dividing them by the total number of points in the array. If it takes 20 data points, then Sum of all array values and divide the total by 20. Smoothing can occur for 2 seconds or any suitable time period, and may require the patient to, for example, raise his or her eyebrows for over 2 seconds in order to make a nurse call. The threshold may be defined as a value from 500-700/1023. If the averaged value is above the threshold, then a call is placed. If not, then there is no call.

The smoothing process can require the patient to raise his or her eyebrows with enough intensity to go over the threshold for at least 20 data points, or about 2 seconds. If the smoothed value is not above the threshold long enough for the average to exceed threshold, then no call is placed.

An alternate path to calibration and signal processing is described below and can be used with, for example, a SNAP® based system as described below. This method can be described as an alternate path for activation of nurse call.

With regard to calibration, the average value may be defined as the sum of the recorded maximum and minimum values during calibration that is then divided by two. For example, a maximum of 748 and a minimum of 150 may be used. Average value may equal (748+150)/2=449. During calibration, a green LED can be lit and inform the care giver, nurse or other clinician to instruct the user to raise their eyebrows 3 times as hard as they can.

Regarding signal processing, two values may be recorded and monitored: the voltage level from the ADC and the average recorded during the calibration sequence. The voltage level ranges from 0-1023 from the ADC and the system may add the values from the ADC. This may be called the total, when the total value (e.g. ADC_1+ADC_2+ . . . ) is above 1-3 multiplied by the average (e.g. 3×449=1347) the nurse call sequence starts with an alert for nurse call initiation by illuminating a red LED and making a beep on/off every 300 milliseconds. Once the total value surpasses 5-15* multiplied by the average value, then a nurse call has been decided by the patient and a call is sent to the base station signified by a red LED that is illuminated for 2 seconds along with a single audio tone for 2 seconds. If the user activates the nurse call but the value does not surpass 5-15 multiplied by the recorded average, no nurse call is placed. (e.g. From the previous example for calculating the average, if the total for the user adds up to 4,290, no nurse call can be placed because the total must exceed 4,490 in order to call the nurse with a confirmation level set at 10 multiplied by the average).

The presently disclosed subject matter can provide a muscle or gesture-controlled alert system. For example, the system may be used for the purpose of nurse call in a hospital setting. In another example, the system may be used for the purpose of alert in a home or rehabilitation facility. In another example, the system may be integrated into the current nurse call/alert/call bell systems. In another example, the system may allow a user to control entire system through a muscle contraction.

In an accordance with an embodiment, the disclosed system may provide feedback, such as visual light and audible tone with 3 modes. The system may show calibration status by indicating a green light illumination for during the calibration sequence of 5 seconds. In an example, action during a call/eyebrow raise may be indicated by one or more of: an audible tone every 300 ms beeps during period over threshold, and a red Light 300 ms pulses for entire period over threshold. Confirmation of nurse call may be indicated by one or more of: an audible tone plays for 2 second at successful call, and a red light illuminating for 2 second corresponding with audible tone.

Wireless transmission from a movement detector may utilize a BLUETOOTH® wireless technique, a Synapse Wireless SNAP®, or another suitable technique. In processing design, signal processing may involve a SNAP module that completes the full signal processing protocol. The movement detector may update a state to the base station (or wall unit). The base station may send one of several different alerts. For example, the alerts may include, but are not limited to, a calibration active alert, a nurse call starting alert, and a nurse call confirmed alert. Status updates on the alert system may include, but are not limited to, a status check of a user node at predetermined intervals (e.g., 10 ms). Sounds may be initiated and a light feedback provided on alerts. With a nurse call confirmed, a contact closure switch mechanism may be activated through a ¼" mono jack, an eight pin DIN connection or another suitable connection to the nurse call system. If not connected to a nurse call system, feedback may be provided to so indicate. A wide area alert via an Internet connection may be activate by sending a text message, calling a phone number, or turning a television station.

In accordance with embodiments, devices may be paired. For example, a movement detector and base station may be paired. Devices may be paired when a movement detector is turned on by removing material between a battery and contact for initializing the detector and connecting to the base station. One light may turn on for indicating that a connection has occurred. For SNAP, this process may be automatic since they can be sent with connection to only their node network from manufacture. For BLUETOOTH® low energy standard (BLE, BLUETOOTH SMART®, or BLUETOOTH® 4.0), there can be control on the base station or wall/alert system side. The detector can be discoverable when turned on, so the alert system can select it and connect. In one embodiment it can be set up prior to being sent out. Only a certain range of detectors may work with a certain alert/wall unit.

Communication ranges between a movement detector and a base station may vary. The range may differ depending on the location and device. The range can be 15 feet or greater, for example. In a hospital setting, there are small areas with more signal noise (Higher signal strength with less range in mind, possible signal attenuation). In care facilities and homes, longer ranges with less signal noise may be the case (Lower overall signal strength but broader signal distribution). In accordance with an embodiment, controls can be implemented by a patient or other user raising his or her eyebrows. Biosensors or other detectors can be used to detect a raised eyebrow. As an example, an electromyography analog circuit may be used. It may have an LT1101 instrumentation amp, a virtual ground, a coin cell battery powered at 3 V, a gain of 280, Ag/AgCl electrodes, and resistive or capacitive electrodes. Detection may be based on accelerometer based movement. Detection may be based on a piezoelectric movement sensor. An electroencephalography sensor system may detect pain.

For eyebrow movement detection, signals from the frontalis muscle may be detected. This system can work on any patient type that is conscious. It may work for severe spinal cord injuries, amyotrophic lateral sclerosis, stroke recovery, Parkinson's disease, Alzheimer's disease, traumatic brain injury, autism, and locked-in syndrome.

In accordance with an embodiment, a movement detector may have a disposable design. It may have an adhesive that lasts at least 1 day. It may have a battery life of at least 1 day. It may be made of recyclable materials.

In accordance with an embodiment, the movement detector component could be a part of a device reclamation system. The device may be sent back to the manufacturing center for disposition for possible recycling of components with a prepaid package included with the device. The protective covering with embedded electrodes may be removed and recycled. The battery may be removed and either recycled or recharged for use in another movement detector. The printed circuit board (PCB) may be disconnected and tested for the ability to be used again and then used in future movement detectors or components may be harvested for future use.

The various techniques described herein may be implemented with hardware or software or, where appropriate, with a combination of both. Thus, the methods and apparatus of the disclosed embodiments, or certain aspects or portions thereof, may take the form of program code (i.e., instructions) embodied in tangible media, such as floppy diskettes, CD-ROMs, hard drives, or any other machine-readable storage medium, wherein, when the program code is loaded into and executed by a machine, such as a computer, the machine becomes an apparatus for practicing the presently disclosed subject matter. In the case of program code execution on programmable computers, the computer will generally include a processor, a storage medium readable by the processor (including volatile and non-volatile memory and/or storage elements), at least one input device and at least one output device. One or more programs may be implemented in a high level procedural or object oriented programming language to communicate with a computer system. However, the program(s) can be implemented in assembly or machine language, if desired. In any case, the language may be a compiled or interpreted language, and combined with hardware implementations.

The described methods and apparatus may also be embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, a video recorder or the like, the machine becomes an apparatus for practicing the presently disclosed subject matter. When implemented on a general-purpose processor, the program code combines with the processor to provide a unique apparatus that operates to perform the processing of the presently disclosed subject matter.

Features from one embodiment or aspect may be combined with features from any other embodiment or aspect in any appropriate combination. For example, any individual or collective features of method aspects or embodiments may be applied to apparatus, system, product, or component aspects of embodiments and vice versa.

While the embodiments have been described in connection with the various embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. A system comprising:
   a movement detector comprising an electromyography device including adhesive coated electrodes that are positioned on to a patient's forehead into an electrode arrangement and used to detect forehead muscle activation indicative of a raised eyebrow of the patient sustained for a time period of at least 2 seconds, and to generate an alert signal only in response to detection of the forehead muscle activation being sustained over a threshold for the time period of at least 2 seconds, wherein the forehead muscle activation is indicative of a desire of the patient to provide a control signal to enable the system to perform a function; and
   a base station interfaced with a nurse call system, wherein the base station wirelessly communicate with the movement detector to receive the alert signal to activate the nurse call system, in response to the received alert signal from the movement detector indicating that the function to be perform is for the base station to activate the nurse call system to indicate that the patient needs assistance.

2. The system of claim 1, wherein the electromyography device comprises one of an adhesive or headband configured to physically locate the electrodes for attachment of the movement detector to a skin surface adjacent to forehead muscles of the patient.

3. The system of claim 2, wherein the forehead muscles can be independently controlled by the patient.

4. The system of claim 1, wherein the movement detector is configured to detect an electrical signal generated by one of contraction and extension of the patient's forehead muscles.

5. The system of claim 4, wherein the electrodes are configured to detect the electrical signal.

6. The system of claim 4,
   wherein the movement detector comprises an amplifier configured to amplify the electrical signal.

7. The system of claim 4, wherein the movement detector is configured to determine minimum and maximum values of the electrical signal, and to use the minimum and maximum values for calibrating detection of forehead muscle movement for implementation of a predetermined action.

8. The system of claim 1, wherein the electrodes are spaced apart from each other.

9. The system of claim 1, wherein the movement detector comprises a wireless radio transmitter configured to wirelessly communicate the alert signal to the base station.

10. The system of claim 9, wherein the movement detector is configured to generate an electrical signal representative of detected movement of the patient's forehead muscles, and
    wherein the wireless radio transmitter is configured to receive the electrical signal, from the movement detector, to generate a digital signal value based on the electrical signal, and to communicate the digital signal value to the base station.

11. The system of claim 1, wherein the movement detector comprises an adhesive configured to physically locate the electrodes and the electrode arrangement, wherein the electrode location material is configured for attachment of the movement detector to a skin surface adjacent to forehead muscles.

12. The system of claim 1, wherein the base station is configured to control the nurse call system to communicate a notification signal based on the alert signal to provide the indication that the patient needs assistance.

13. The system of claim 1, wherein the base station comprises a light emitter configured to emit light based on the alert signal.

14. The system of claim 1, wherein the base station comprises at least one processor and memory configured to:
    wirelessly receive the alert signal;
    apply an algorithm to data contained within the alert signal; and
    control implementation of a predetermined action based on an application of the algorithm to the data.

15. The system of claim 1, wherein the movement detector is configured to calibrate forehead muscle movement detection during a startup mode.

16. The system of claim 1, wherein the movement detector is configured to receive user input for activation.

17. A method comprising:
    using an electromyography device including adhesive coated electrodes that are positioned into an electrode arrangement placed near forehead muscles of a patient to detect forehead muscle activation indicative of a raised eyebrow of the patient sustained for a time period of at least 2 seconds;
    generating an alert signal only in response to detection of the forehead muscle activation being sustained over a threshold for the time period of at least 2 seconds, wherein the forehead muscle activation is indicative of a desire of the patient to provide a control signal to enable the system to perform a function,
    at a base station located remote from the electromyography device that is interface with a nurse call system, wherein the base station wirelessly communicate with the movement detector to receive the alert signal to activate the nurse call system, in response to the received alert signal from the movement detector indicating that the function to be perform is for the base station to activate the nurse call system to indicate that the patient needs assistance.

18. The method of claim 17, wherein the electromyography device comprises an adhesive for attachment of the movement detector to a skin surface adjacent to the forehead muscles to detect movement of the forehead muscles,
    wherein detecting movement of the forehead muscles comprises using the movement detector to detect the movement of the forehead muscles.

19. The method of claim 18, wherein the forehead muscles can be independently controlled by the user.

20. The method of claim 18, wherein detecting movement of the forehead muscles comprises detecting an electrical signal generated by one of contraction and extension of the forehead muscles.

21. The method of claim 17, further comprising using the electrodes to detect an electrical signal.

22. The method of claim 21, further comprising using a plurality of spaced-apart electrodes to detect the electrical signal.

23. The method of claim 21, further comprising:
    determining minimum and maximum values of the electrical signal; and
    using the minimum and maximum values for the calibrating forehead muscle movement detection for implementation of a predetermined action.

24. The method of claim 17, wherein using the electromyography device comprises detecting an electrical signal generated by one of contraction and extension of the forehead muscles, and wherein the method further comprises amplifying the electrical signal.

25. The method of claim 17, further comprising using a wireless radio transmitter to communicate the alert signal to the base station.

26. The method of claim 25, further comprising:

generating an electrical signal representative of detected movement of the forehead muscles by the movement detector;

generating a digital signal value based on the electrical signal; and communicating the digital signal value to the base station.

27. The method of claim 17, further comprising emitting light based on the alert signal.

28. The method of claim 17, further comprising:

applying an algorithm to data contained within the alert signal; and controlling implementation of a predetermined action based on an application of the algorithm to the data.

29. The method of claim 17, further comprising calibrating forehead muscle movement detection during a startup mode.

30. The method of claim 17, further comprising receiving user input for activation.

\* \* \* \* \*